(12) United States Patent
Pascal-Moussellard et al.

(10) Patent No.: US 11,154,339 B2
(45) Date of Patent: Oct. 26, 2021

(54) BONE STABILIZATION IMPLANT WITH ANCHOR SCREW LOCKING ELEMENT

(71) Applicant: ORTHOPAEDIC & SPINE DEVELOPMENT (OSD), Avignon (FR)

(72) Inventors: Hugues Pascal-Moussellard, Paris (FR); Paolo Mangione, Bordeaux (FR)

(73) Assignee: Orthopaedic & Spine Development (OSD), Avignon (FR)

( * ) Notice: Subject to any disclaimer, the term of this patent is extended or adjusted under 35 U.S.C. 154(b) by 140 days.

(21) Appl. No.: 16/527,474

(22) Filed: Jul. 31, 2019

(65) Prior Publication Data
US 2020/0038078 A1     Feb. 6, 2020

(30) Foreign Application Priority Data

Jul. 31, 2018  (FR) ...................... 1857157

(51) Int. Cl.
*A61B 17/80*  (2006.01)
*A61B 17/70*  (2006.01)

(52) U.S. Cl.
CPC ...... *A61B 17/8052* (2013.01); *A61B 17/7007* (2013.01); *A61B 17/7059* (2013.01); *A61B 17/8061* (2013.01); *A61F 2230/0093* (2013.01)

(58) Field of Classification Search
CPC ............ A61B 17/8052; A61B 17/7007; A61B 17/7059; A61B 17/8061; A61B 17/8042; A61F 2230/0093
See application file for complete search history.

(56) References Cited

U.S. PATENT DOCUMENTS

| 2005/0027298 | A1 | 2/2005 | Michelson |
| 2005/0177161 | A1 | 8/2005 | Baynham et al. |
| 2008/0021470 | A1 | 1/2008 | Ross |
| 2008/0091206 | A1 | 4/2008 | Johnson |
| 2017/0065311 | A1 | 3/2017 | George et al. |
| 2018/0103989 | A1 | 4/2018 | Altarac et al. |

FOREIGN PATENT DOCUMENTS

| EP | 1520545 | 4/2005 |
| FR | 2778088 | 11/1999 |
| FR | 2810532 | 12/2001 |
| FR | 2924015 | 5/2009 |
| FR | 2949317 | 3/2011 |
| WO | 1998034553 | 8/1998 |

OTHER PUBLICATIONS

European Search Report for French application 1857157, dated Jun. 28, 2019.

*Primary Examiner* — Jerrah Edwards
*Assistant Examiner* — Jared Klar Rovira
(74) *Attorney, Agent, or Firm* — Burris Law, PLLC

(57) ABSTRACT

A bone stabilization implant includes a stabilization plate provided with anchor orifices intended to receive bone anchor screws and a locking element secured in rotation to a pivot shaft pivotally mounted in a bore of the plate and movable between a rest position and a locking position of the bone anchor screw. The locking element is integrally disposed inside a recess and its lower face has a central area bearing on a bottom wall of the recess and at least one peripheral area adapted to at least partially cover an anchor orifice in the locking position. The lower face has a convex shape according a radial axis extending radially to its peripheral area.

20 Claims, 8 Drawing Sheets

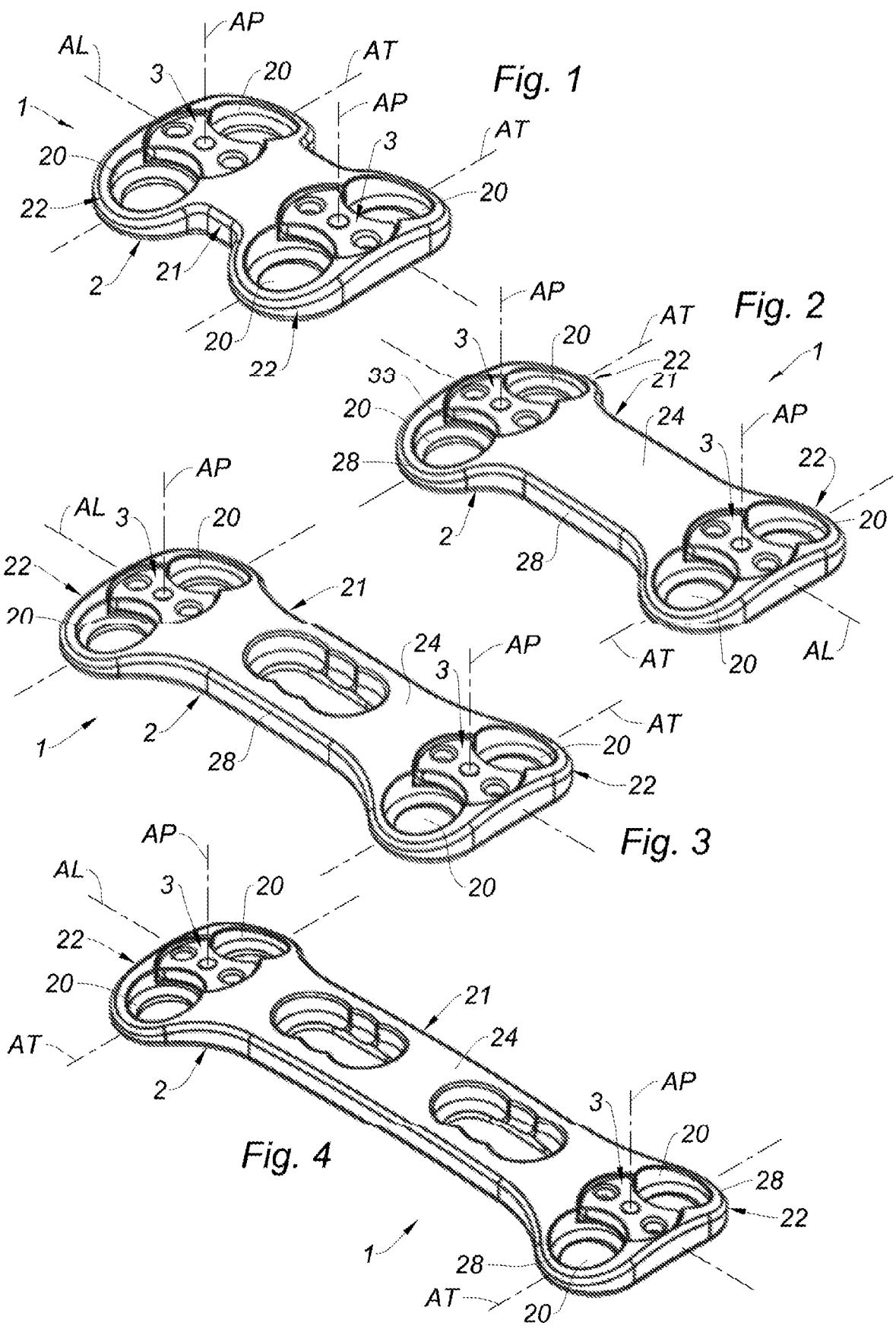

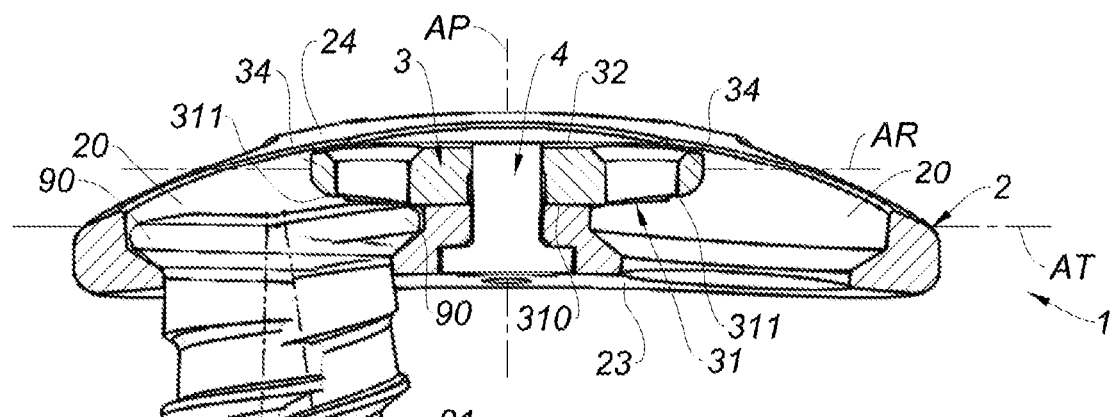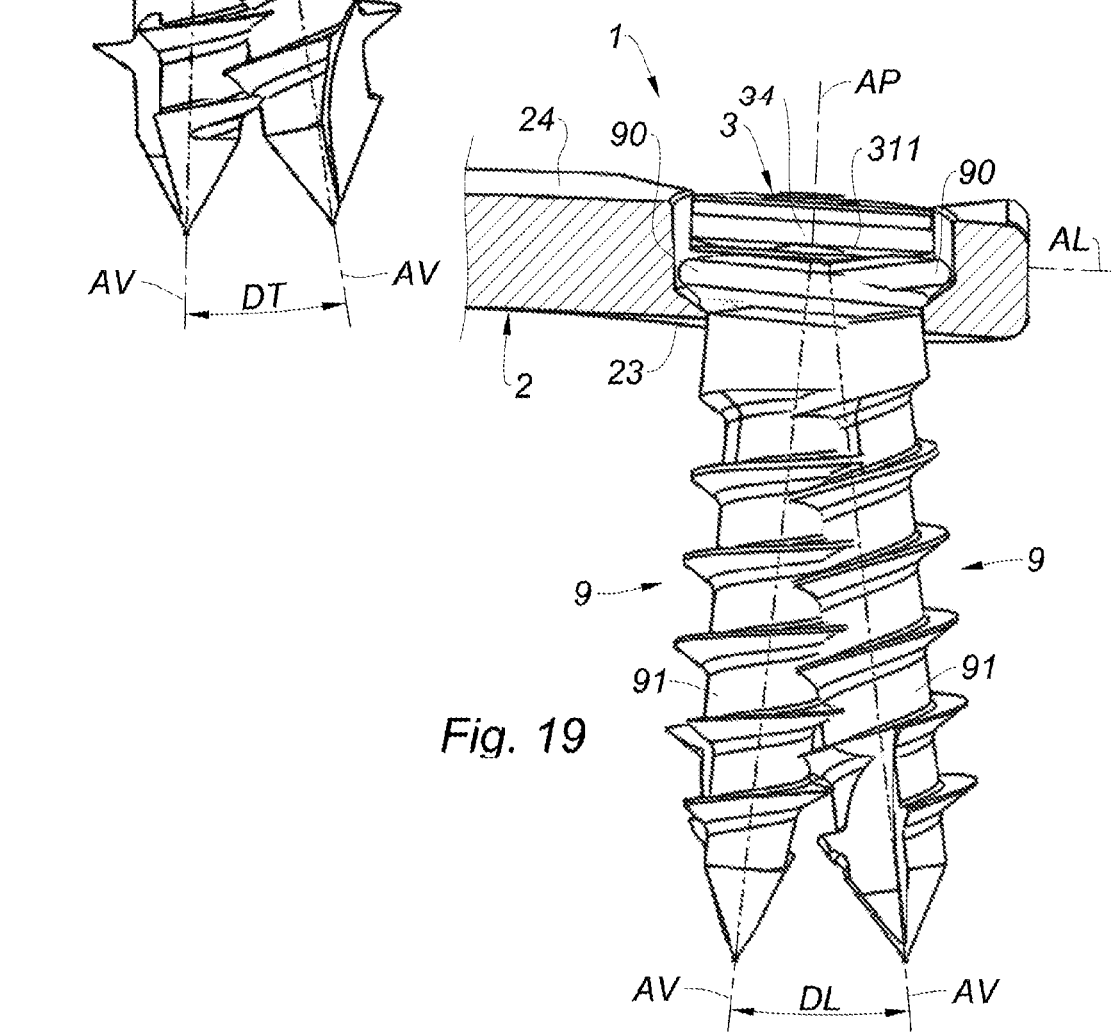
Fig. 18
Fig. 19

BONE STABILIZATION IMPLANT WITH ANCHOR SCREW LOCKING ELEMENT

CROSS-REFERENCE TO RELATED APPLICATIONS

This application claims priority to and the benefit of FR 18/57157 filed on Jul. 31, 2018. The disclosure of the above application is incorporated herein by reference.

FIELD

The present disclosure relates to a bone stabilization implant for stabilizing at least two bone structures.

BACKGROUND

The statements in this section merely provide background information related to the present disclosure and may not constitute prior art.

After implantation and screwing of bone anchor screws into the bone structures, various reasons (e.g., mechanical stresses in the bone structures, bone degeneration, insufficient bone quality, anatomical difficulty, bad implantation of the screws) may cause a bone anchor screw to lose the bone anchorage thereof and then back out from an anchor orifice of the stabilization plate ("backing-out" phenomenon) at the risk of injuring the adjacent organs, such as the esophagus or trachea in the case of an anterior cervical spine stabilization implant.

It is therefore known to provide locking of the bone anchor screws in order to inhibit them from backing out from the stabilization plate.

The document FR2949317A proposes a bone screw lock in the form of a non-return lip inside the anchor orifice which cooperates with a shoulder on the periphery of the anchor screw, with the drawbacks of making the lock complex to produce and also limiting the inclination of the anchor screw which must necessarily be aligned to be able to cooperate with the non-return lip, not to mention the difficulty to remove the anchor screw if necessary.

The document FR2924015A proposes a bone screw lock in the form of a slot opening both into the anchor orifice and into an edge of the stabilization plate in order to provide an elastic deformation capability which would provide a retention of the anchor screw in the anchor orifice, with the drawbacks of weakening the stabilization plate and having sharp ridges in the edge of the stabilization plate, at the level of the slot, thus risking injuring the adjacent tissues.

The document FR2810532A proposes a bone screw lock in the form of a split ring, common to at least two anchor orifices, which can be handled by a tool likely to be retracted and thus enable the passage of the anchor screws and which naturally returns to a deployed configuration in order to lock the anchor screws, with the drawback that the surgeon must handle the split ring with the tool while setting the anchor screws which makes the setup of the anchor screws particularly complex.

Each of the documents FR2778088A and US2005/0177161A1 proposes a bone screw lock in the form of a sliding drawer which partially covers at least one anchor screw, with the drawback of limiting the inclination of the anchor screw which must follow a specific orientation to let the drawer slide towards its locking position.

The document US2005/0027298A1 proposes a bone screw lock in the form of a locking element associated with two anchor orifices and screwed into the stabilization plate, this locking element having a circular shape with two lateral cutouts, where these lateral cutouts may coincide with the anchor orifices to enable the passage of the anchor screws, before pivoting the locking element by screwing to lock the anchor screws. Moreover, this locking element is integrally disposed inside a recess provided on the outer face of the stabilization plate such that the locking element does not protrude above the outer face of the stabilization plate. Furthermore, this locking element has a lower face, facing the anchor orifices, which is planar in order to bear flat on the bottom of the recess, and the holding of the locking element is provided by a complete screwing of the locking element until its lower face bears on the flat bottom of the recess. This type of bone screw lock has the drawback that it requires a screwing operation of the locking element, which considerably lengthens the operating time and requires additional difficult gestures to screw accurately. Moreover, this bone screw lock limits the inclination of the anchor screw which must follow a specific orientation to let the locking element go down (during the screwing thereof) until it abuts against the bottom of the recess.

The document US2008/0027298A1 proposes a bone screw lock in the form of a locking element mounted only pivotally on the stabilization plate, between a rest position in which the locking element completely uncovers the associated anchor orifice and a locking position in which the locking element at least partially covers the associated anchor orifice. This locking element has a concave lower face, which conforms to the convex shape of the outer face of the stabilization plate, this locking element being indeed pivotable on this outer face while projecting above this outer face of the stabilization plate, with the drawback of forming a protrusion that may injure the adjacent tissues.

The document US2018/0103989A1 proposes a bone screw lock in the form of a locking element screwed into a bushing, this bushing being pivotally mounted in the stabilization plate. Also, because of this screwing, the locking element can be pivoted in one direction and only a quarter turn, to inhibit it from unscrewing, and abutments are provided to stop it in the anchor screw locking position thereof. To the extent that these anchor screws are monoaxial, that is to say that they are implantable according to a fixed screwing axis without possible angular displacement, this locking element screwed into its bushing operates properly, but it would not be suitable for polyaxial anchor screws, that is to say implantable according to a fixed screwing axis with a possible angular displacement at 360 degrees. Moreover, this locking element projects above this outer face of the stabilization plate, at the risk of injuring the adjacent tissues.

The document EP 1 520 545 proposes a locking element secured to a shaft pivotally mounted on the stabilization plate in an oblong hole, where this shaft has an oblong lock opposite to the locking element such that by aligning the oblong lock and the oblong hole it is possible to insert the shaft into the oblong hole, and by misaligning the oblong lock and the oblong hole the shaft is then locked in translation. Also, because of this principle of mounting in an oblong hole, the locking element can be pivotable only within a certain limit, and certainly not at 180 degrees at the risk of aligning the oblong hole and the oblong lock and thus disassembling the shaft. Thus, such a locking element would not be suitable for polyaxial anchor screws. Moreover, this locking element has a planar lower face, which is also not suitable for polyaxial anchor screws.

SUMMARY

The present disclosure provides a bone stabilization implant provided with a lock for locking the bone anchor screws, where such lock will be particularly barely traumatic for the adjacent tissues.

The present disclosure also provides a bone anchor screw lock (also referred to herein simply as a "bone screw lock") which enables a polyaxiality of the bone anchor screw(s) in particular with degrees of freedom in inclination (in other words angular displacements) both longitudinally and transversely.

The present also disclosure provides a stabilization implant with a particularly anatomical and atraumatic stabilization plate, while receiving the bone screw lock.

The present also disclosure provides bone screw locks which are simple in design and which provide a reversible locking allowing for an easy switching from the rest position into the locking position and vice versa.

To this end, the present disclosure provides a bone stabilization implant for stabilizing at least two bone structures, said bone stabilization implant comprising:

a stabilization plate provided with an inner face intended to be in contact with the bone structures and an opposite outer face, with at least two anchor orifices which pass through said stabilization plate from the inner face to the outer face, said anchor orifices being intended to receive bone anchor screws for anchorage in the bone structures;

at least one locking element associated with two anchor orifices aligned according to a transverse axis, said locking element being pivotally mounted on the outer face of the stabilization plate about a pivot axis orthogonal to the transverse axis, between a rest position in which the locking element completely uncovers the two associated anchor orifices and a locking position in which the locking element at least partially covers the two associated anchor orifices, in place, to lock the bone anchor screws in said two anchor orifices and thus inhibit the bone anchor screws from coming out beyond the outer face of the stabilization plate, and in which said locking element has a lower face facing the associated anchor orifice and an opposite upper face;

wherein:

each of the two anchor orifices is at least internally delimited, starting from the outer face to the inner face, successively by an inlet portion with a cylindrical shape followed by a bearing face shaped as a spherical or frustoconical portion to enable a bearing with polyaxiality to the corresponding bone anchor screw;

the locking element is mounted only pivotally about the pivot axis being secured in rotation to a pivot shaft pivotally mounted in a bore formed in the stabilization plate, said locking element being pivotable at 360 degrees in two opposite directions of rotation about the pivot axis;

the locking element is integrally disposed inside a recess provided on the outer face of the stabilization plate such that the locking element does not protrude above the outer face of the stabilization plate irrespective of its position;

the locking element is locked in translation in two opposite directions of translation along the pivot axis, this pivot shaft having a head which abuts against an inner shoulder provided in the bore as well as a rod which passes through a bottom wall of the recess without projecting from the outer face of the stabilization plate, and on which is fastened the locking element;

the recess opens into the inlet portions of the two anchor orifices such that, in the locking position, the locking element extends into the inlet portions of the two anchor orifices, above the bearing faces of the two anchor orifices;

the lower face of the locking element has a central area bearing on the bottom wall of the recess and crossed by the rod of the pivot shaft, and said lower face has two peripheral areas adapted to at least partially cover the two respective associated anchor orifices in the locking position, said two peripheral areas extending from the central area to respective flanges, according to two respective radial axes extending radially from the pivot axis; and the two peripheral areas of the lower face of the locking element have a convex shape according to both respective radial axes from the central area to the respective flanges such that, in the rest position, each of the two peripheral areas of the lower face deviates from the bottom wall of the recess starting from the central area which is in contact with said bottom wall to the flanges which are deviated from said bottom wall;

the two peripheral areas of the lower face of the locking element have, according to each of the two radial axes, a second radius of curvature.

Thus, with this convex shape of the two peripheral areas of the lower face of the locking element, according to the second radius of curvature, and with this integral arrangement inside a recess, the locking element, purely rotary at 360 degrees, is adapted to overlap of the anchor screw which can have different inclinations due to this convexity.

Depending on the inclination of the bone anchor screws (each being in polyaxial bearing), the locking element can be rotated in one direction (clockwise direction) or in the other (counterclockwise direction) in order to dock the anchor screws on a favorite side and thus have the peripheral areas in position to lock the anchor screws for an efficient locking.

Moreover, this convexity of each of the two peripheral areas of the lower face of the locking element (according to the second radius of curvature) will contribute to a slight elastic bending of the locking element, to keep it stable in the locking position, while integrating into the thickness of the stabilization plate, that is to say that the locking element does not protrude above the outer face of the stabilization plate. The present disclosure therefore allows using an elasticity stored by the locking element to provide self-stability in the locking position on the bone anchor screw(s).

Advantageously, the second radius of curvature on both peripheral areas, along the respective radial axes, is comprised between 5 and 20 millimeters.

This value of the second radius of curvature is advantageous for a stable holding in the locking position irrespective of the angular displacements of the bone anchor screws.

In a particular form, the central area has a convex or concave shape according to a first radius of curvature, where the second radius of curvature is smaller than the first radius of curvature.

Advantageously, the first radius of curvature is comprised between 30 and 60 millimeters.

According to an advantageous form, the lower face of the locking element has a symmetry of revolution about the pivot axis.

Thus, the convexity of the peripheral areas of the lower face of the locking element is symmetrical about the pivot axis, which is advantageous for the locking element to dock the anchor screws in one direction (clockwise direction) or in the other (counterclockwise direction).

In a particular form, the flanges of the lower face form rounded chamfers, in the continuation of the two peripheral areas, having a third radius of curvature which is smaller than the second radius of curvature.

Advantageously, the third radius of curvature is comprised between 0.4 and 1 millimeter.

In a particular form, the lower face extends over a given main distance starting from the pivot axis, and along each radial axis, and successively has:

the central area which extends from the pivot axis along the radial axis, over a given central distance such that the ratio of the central distance to the main distance is comprised between 0.1 and 0.3;

the peripheral area which extends from the central area along the radial axis, over a peripheral distance such that the ratio of the peripheral distance to the main distance is comprised between 0.5 and 0.7;

the flange which extends from the peripheral area along the radial axis, over an edge distance such that the ratio of the edge distance to the main distance is comprised between 0.1 and 0.2;

and where the main distance is equivalent to the sum of the central distance, the peripheral distance and the edge distance.

Thus, the peripheral area is the area which occupies the largest distance and which gives the convex shape to the lower face.

According to one feature, the stabilization plate is made of an implantable biocompatible material that has sufficient strength characteristics to obtain a safe stabilization of the bone structures prior to fusion. As a non-limiting example, this material is a titanium alloy or any other metallic or polymeric material having the desired characteristics.

According to one feature, when measuring a thickness of the locking element between its lower face and its upper face, the thickness of the locking element decreases along the two radial axes and from the central area of the lower face, then along the peripheral areas to the flanges of the lower face, such that the locking element is thinned at the level of the flanges.

This thinning along the two radial axes, coming closer to the peripheral areas, and coming closer to the flanges of the locking element, will contribute to improving the above-mentioned elastic flexibility aspect.

According to another feature, the upper face of the locking element has a convex shape according to both radial axes.

According to an advantageous form, the upper face of the locking element has a symmetry of revolution about the pivot axis.

According to a first possibility, the two peripheral areas of the lower face of the locking element are disposed diametrically opposite to each other on either side of the pivot axis, such that the two radial axes starting from the pivot axis to both respective peripheral areas are coincident.

In this first possibility, the locking element pivots about 90 degrees to switch from a rest position into a locking position, and vice versa.

In this first possibility, it is advantageous that the pivot axis intersects the transverse axis.

According to a second possibility (alternatively to the above-mentioned first possibility), the two peripheral areas of the lower face of the locking element are disposed on either side of a midplane passing through the pivot axis and orthogonal to the transverse axis without being diametrically opposite to each other, such that the two radial axes starting from the pivot axis to both respective peripheral areas form a non-zero angle at their intersections on the pivot axis.

In this second possibility, the locking element pivots by about 180 degrees to switch from a rest position into a locking position, and vice versa.

In this second possibility, the pivot axis is away from the transverse axis.

According to another possibility of the present disclosure, the stabilization plate has an elongated shape according to a longitudinal axis, and the inner face of the stabilization plate is concave according to this longitudinal axis and the outer face of the stabilization plate is convex according to this longitudinal axis.

Thus, the stabilization plate has an elongated shape and has a double curvature, namely a curvature in the longitudinal direction and another curvature in the transverse direction, both curvatures having the same direction because one is convex and the other is concave.

According to another possibility of the present disclosure, the transverse axis is orthogonal to the longitudinal axis and to the pivot axis, and the inner face of the stabilization plate is concave according to this transverse axis and the outer face of the stabilization plate is convex according to this transverse axis.

Advantageously, the inner face of the stabilization plate has an inner radius of curvature according to the transverse axis and the outer face of the stabilization plate has an outer radius of curvature according to the transverse axis, where the outer radius of curvature is smaller than the inner radius of curvature, and when measuring a thickness of the stabilization plate between its inner face and its outer face and considering a longitudinal plane of symmetry which includes the longitudinal axis and which is orthogonal to the transverse axis, the thickness of the stabilization plate varies symmetrically on either side of said longitudinal plane of symmetry and decreases according to the transverse axis and starting from the longitudinal plane of symmetry to both respective longitudinal borders of the stabilization plate, such that the stabilization plate is thinned at the level of both longitudinal borders thereof.

Thus, in the transverse direction, the radius of curvature is larger on the inner face than on the outer face of the stabilization plate, which causes a continuous variation in thickness of the stabilization plate in the transverse direction, with a maximum thickness at the center and a minimum on the longitudinal borders of the stabilization plate.

According to one variant, the longitudinal dimension of the stabilization plate is 2 to 7 times larger than the largest transverse dimension of the stabilization plate.

In accordance with another advantageous feature of the present disclosure, the locking element is provided with two holes on its upper face to enable a handling and a pivoting by a tool.

The present disclosure also concerns the feature according to which the bone stabilization implant is a cervical spine stabilization implant.

The present disclosure also relates to a bone stabilization system for stabilizing at least two bone structures, said bone stabilization system comprising at least:

one bone stabilization implant according to the present disclosure; and at least two bone anchor screws, with a bone anchor screw per anchor orifice formed in the stabilization plate of the bone stabilization implant, where the bone anchor screws can:

be inserted into the anchor orifices when the locking element is in the rest position; and be locked in the anchor orifices and thus be inhibited from coming out beyond the outer face of the stabilization plate when the locking element is in the locking position;

in which each of the bone anchor screws has a head having a spherical bearing surface to bear with polyaxiality on the bearing face of the concerned anchor orifice, and a threaded rod adapted to be anchored in the concerned bone structure and extending according to a screwing axis, such that the bone anchor screws have angular displacements of their respective screwing axes at 360 degrees, and in which the locking element provides a locking of the two bone anchor screws irrespective of the angular displacements of their respective screwing axes.

According to one possibility, the bone anchor screws have angular displacements comprised between 5 to 15 degrees at most.

In other words, the screwing axes of the bone anchor screws can be inclined, with respect to a neutral position, by plus or minus 5 to 15 degrees; the neutral position of a bone anchor screw corresponding to a position in which the screwing axis coincides with an axis of symmetry of the bearing face shaped as a spherical or frustoconical portion of the corresponding anchor orifice.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which:

FIGS. 1 to 4 are schematic perspective views of four variations of a bone stabilization implant according to a first form of the present disclosure, with four different implant sizes;

Figure 12:
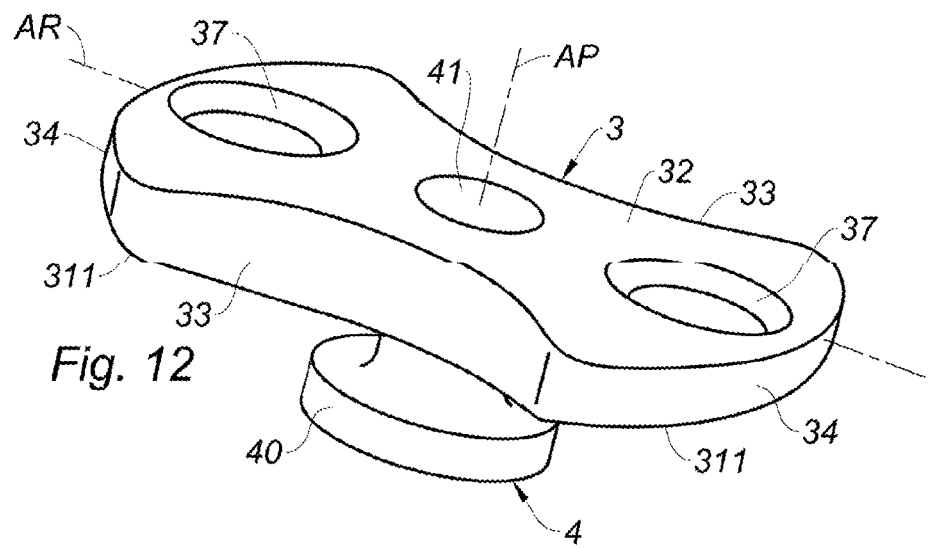
FIG. 12 is a schematic perspective view of a locking element secured to its pivot shaft, as used in the bone stabilization implants of FIGS. 1 to 8 according to the first form of the present disclosure.
Figure 13:
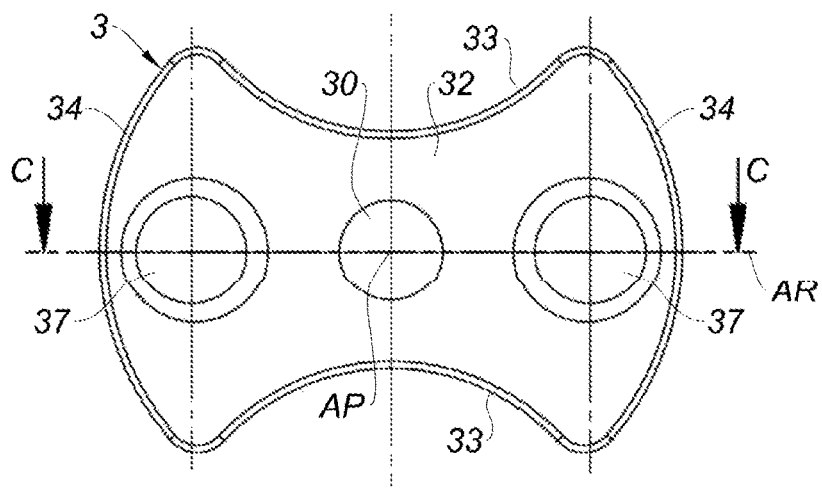
FIG. 13 is a schematic top view of the locking element alone without its pivot shaft of FIG. 12.
Figure 17:
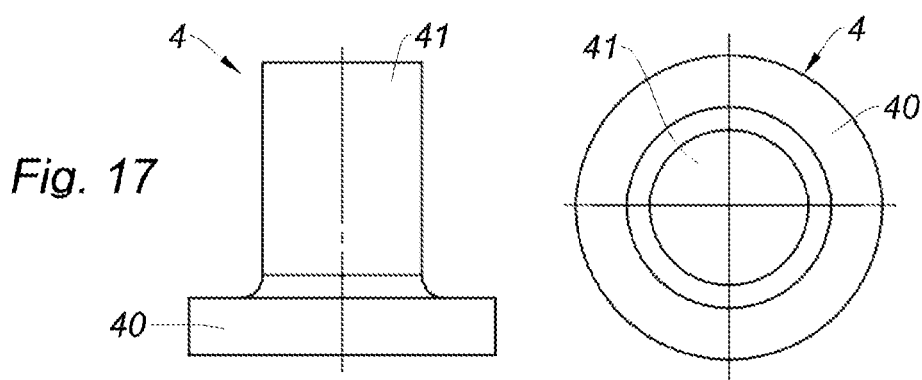
Figure 20:
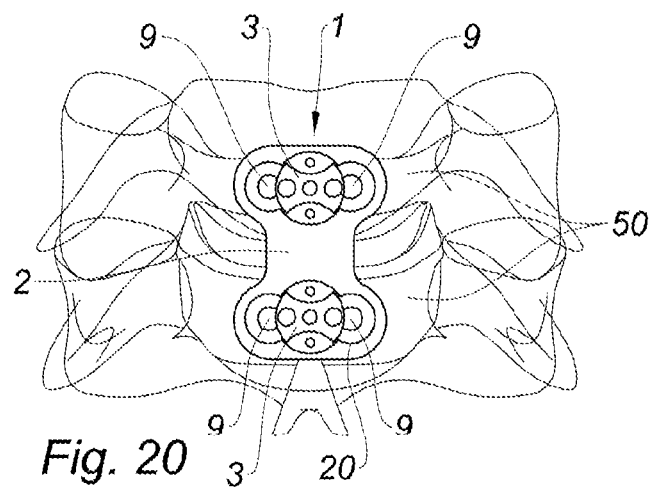
Figure 21:
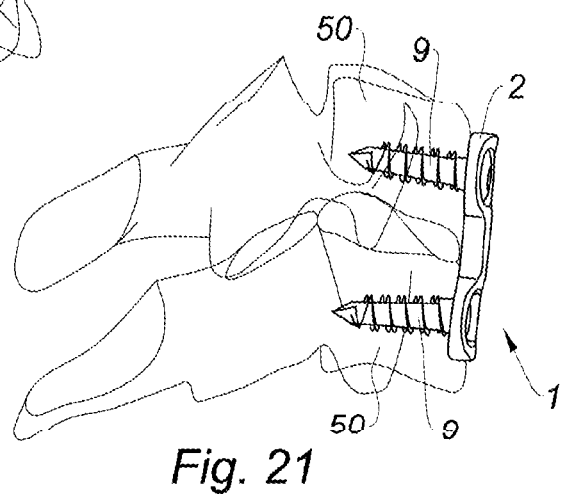
Figure 22:
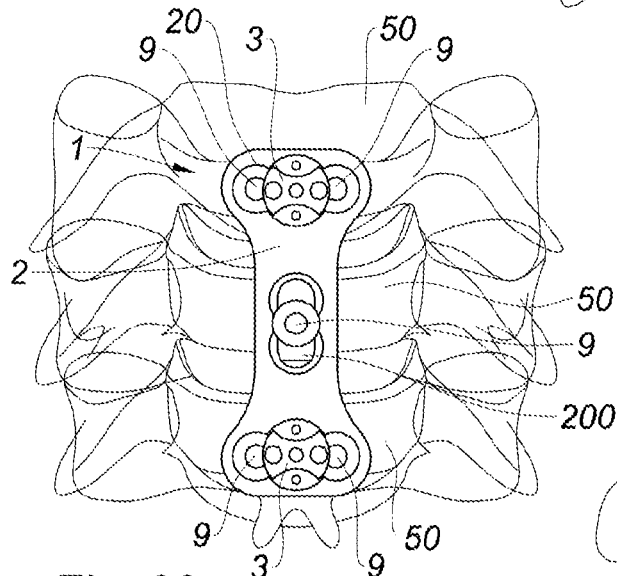
Figure 23:
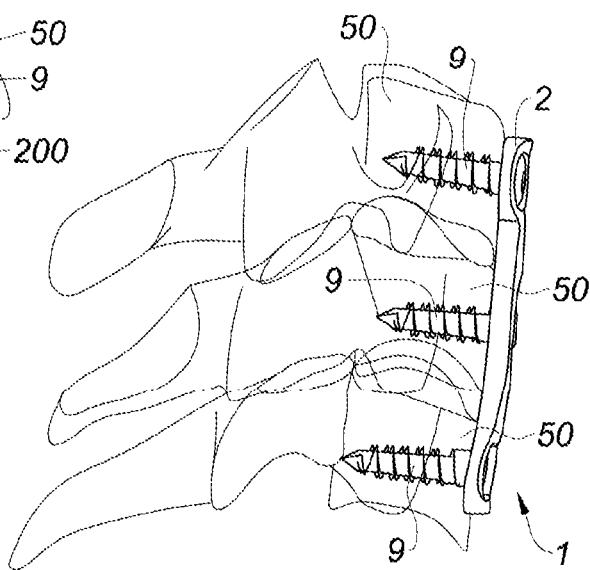
Figure 24:
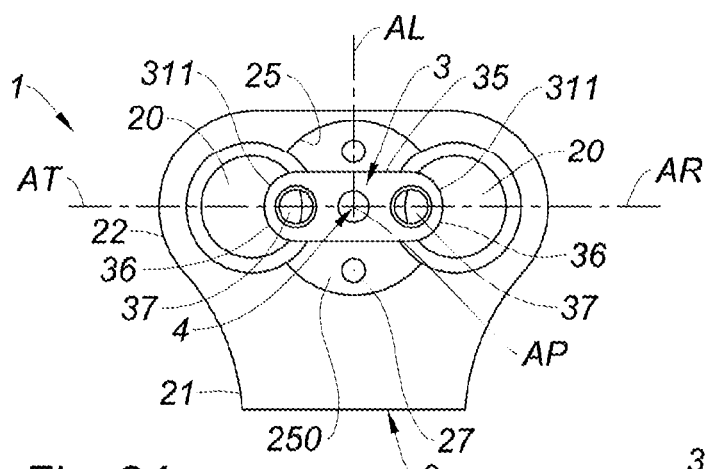
Figure 25:
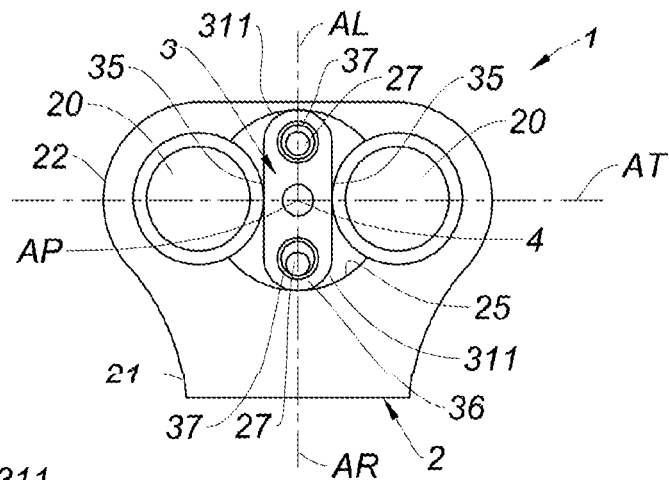
Figure 26:
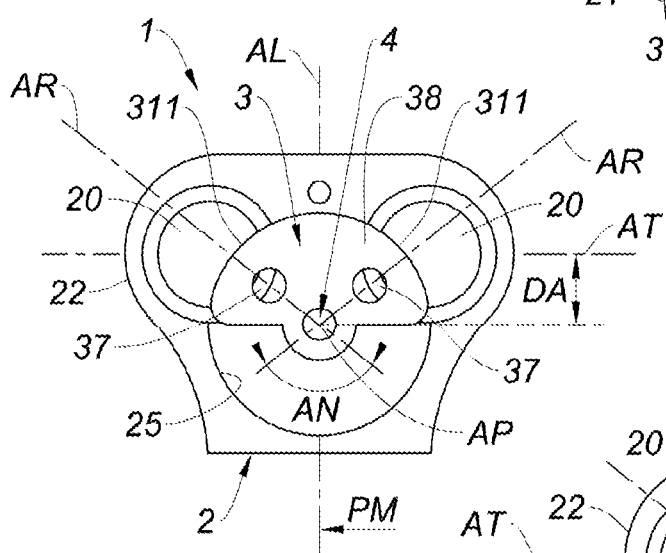
Figure 27:
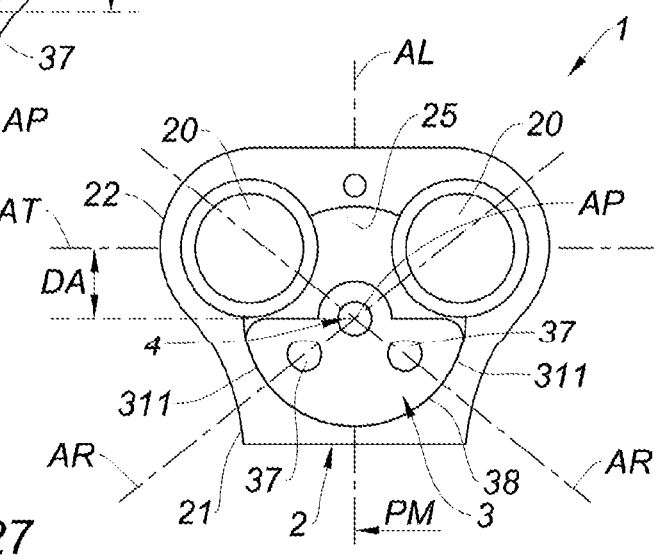

FIG. 17 comprises a schematic side (to the left) and top (to the right) view of the pivot shaft alone of FIG. 12;

FIGS. 18 and 19 are schematic partial and cross-sectional (FIG. 18) and longitudinal sectional (FIG. 19) views of the bone stabilization implant of FIGS. 1 to 8 according to the first form of the present disclosure, with a locking element in the locking position of a bone anchor screw which is illustrated in both figures in two distinct orientations, in a neutral position and in a position at the maximum of the longitudinal (FIG. 18) or transverse (FIG. 19) angular displacement thereof;

FIGS. 20 and 21 are schematic views of the bone stabilization implant of FIG. 1 implanted on two vertebrae of a cervical spine with bone anchor screws, with an anterior view (FIG. 20) and a lateral view (FIG. 21);

FIGS. 22 and 23 are schematic views of the bone stabilization implant of FIG. 3 implanted on two vertebrae of a cervical spine with bone anchor screws, with an anterior view (FIG. 22) and a lateral view (FIG. 23);

FIGS. 24 and 25 are schematic partial top views of a bone stabilization implant according to a second form of the present disclosure, with a locking element in the locking position (FIG. 24) and in the rest position (FIG. 25); and FIGS. 26 and 27 are schematic partial top views of a bone stabilization implant according to a third form of the present disclosure, with a locking element in the locking position (FIG. 26) and in the rest position (FIG. 27).

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

The following detailed description covers several forms of a bone stabilization implant 1 according to the present disclosure, and in the following description, and in all figures, identical or similar reference numerals designate identical or similar members, set of members, functional elements or structural elements.

In the examples illustrated and described hereinafter, the bone stabilization implant 1 is a cervical spine stabilization implant, and in particular for stabilizing at least two bone structures such as vertebrae of the cervical spine.

This bone stabilization implant 1 is in particular an anterior implant intended to be affixed to the anterior faces of two or several vertebrae of the cervical spine, to achieve stabilization or fusion of these two or several vertebrae.

With reference to FIGS. 1 to 6 and also to FIGS. 24 to 27, the bone stabilization implant 1 comprises a stabilization plate 2 in which anchor orifices 20 are formed which pass through the stabilization plate 2, where these anchor orifices 20 are intended to receive bone anchor screws 9 (shown in FIGS. 18 to 23) for anchorage in the bone structures 50 such as vertebrae of a cervical spine as shown in FIGS. 20 to 23.

This bone stabilization implant 1 further comprises at least one locking element 3 associated with at least one anchor orifice 20, where this locking element 3 is pivotally mounted on the stabilization plate 2 about a pivot axis AP between:

a rest position (shown in FIGS. 1 to 5, 25 and 27) in which the locking element 3 completely uncovers the associated anchor orifice(s), in order to enable the insertion of the bone anchor screw(s) 9 into the anchor orifice(s) 20; and a locking position (shown in FIGS. 6, 24 and 26) in which the locking element 3 at least partially covers the associated anchor orifice(s), in place, to lock the bone anchor screw(s)

9 in the anchor orifice(s) 20 and thus inhibit the bone anchor screw(s) 9 from inadvertently coming out beyond the stabilization plate 2.

In the illustrated examples, the stabilization plate 2 has an elongated shape according to a longitudinal axis AL and has a central portion 21 bordered by two end portions 22 in which are formed respectively two anchor orifices 20 aligned according to a transverse axis AT orthogonal to the pivot axis AP and to the longitudinal axis AL.

On each end portion 22 is provided a locking element 3 which is associated with the two anchor orifices 20 of the end portion 22, such that each locking element 3 is pivotally mounted on the concerned end portion 22 of the stabilization plate 2 between:

a rest position (shown in FIGS. 1 to 5, 25 and 27) in which the locking element 3 completely uncovers the two associated anchor orifices 20; and a locking position (shown in FIGS. 6, 24 and 26) in which the locking element 3 at least partially covers the two associated anchor orifices 20.

The stabilization plate 2 is provided with an inner face 23 intended to be in contact with the bone structures 50 and an opposite outer face 24, and the anchor orifices 20 pass through the stabilization plate 2 from the inner face 23 to the outer face 24.

As shown in FIGS. 1 to 4, the stabilization plate 2 and particularly its central portion 21 may have different lengths along the longitudinal axis AL, depending on the spacing between the bone structures 50 and/or according to the number of bone structures 50 on which the stabilization plate 2 will be anchored.

As shown in FIGS. 3, 4 and 22, it is also possible to provide on the central portion 21 with one or several central anchor orifice(s) 200, passing through the stabilization plate 2 from the inner face 23 to the outer face 24, for receiving bone anchor screws 9 in addition to those that will be present in the anchor orifices 20.

Each anchor orifice 20 is at least internally delimited, starting from the outer face 24 to the inner face 23, successively by:

an inlet portion 201 with a cylindrical shape; followed by a bearing face 202 shaped as a spherical or frustoconical portion to enable a bearing with polyaxiality to the corresponding bone anchor screw 9.

Each anchor orifice 20 has a symmetry of revolution about a central axis, which thus forms an axis of symmetry of the bearing face 202.

For such a polyaxiality to the bone anchor screw 9, each of these bone anchor screws 9 has a head 90 having a spherical bearing surface to bear against the bearing face 202 of an anchor orifice 20, and a threaded rod 91 adapted to be anchored in the concerned bone structure 50 and extending according to a screwing axis AV.

These anchor orifices 20 are oriented simultaneously radially in the transverse direction, and outwardly in the longitudinal direction, so that the fastening of the stabilization plate 2 causes a bone compression. In other words, these anchor orifices 20 have an axis inclined longitudinally by an external angle (such that the bone anchoring members 9 will have a compressive effect when they are set in place) and transversely at an internal angle (such that the force of anchorage by screwing is perpendicular to the bone surface and therefore maximum).

In addition, each anchor orifice 20 has a bearing face 202 shaped as a spherical or frustoconical portion which is preferably oriented according to the aforementioned inclined axis, to cooperate with the congruent bearing surface of the bone anchor screw 9, thus ensuring a force evenly distributed over the stabilization plate 2.

The central portion 21 has a width (dimension considered parallel to a transverse axis AT) which is smaller than the width of the end portions 22. In other words, the end portions 22 are widened with respect to the central portion 21, to form the two anchor orifices 20 in each end portion 22.

Figure 7:
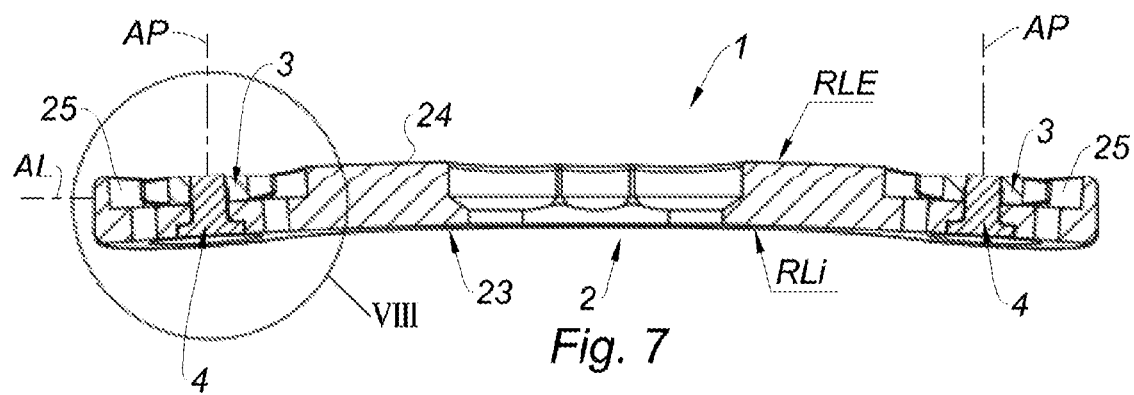
FIG. 7 is a schematic longitudinal sectional view of the bone stabilization implant of FIG. 6 according to the section plane VII-VII.
Figure 10:
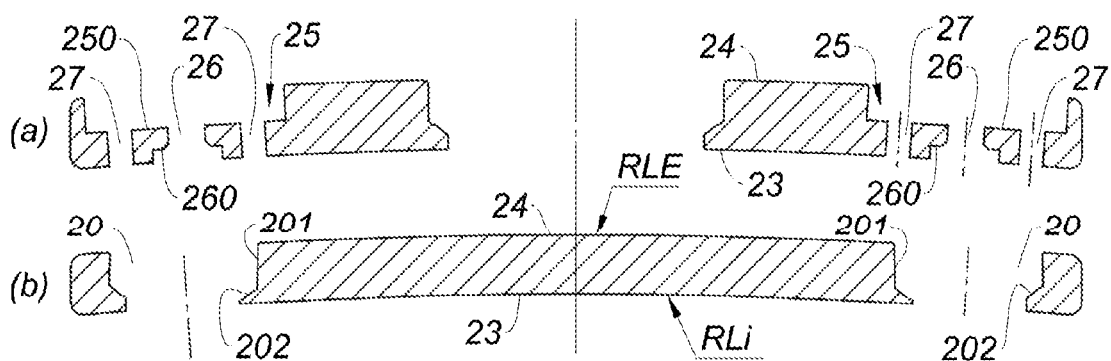
FIG. 10 is a schematic longitudinal sectional view of the bone stabilization implant of FIG. 9 according to the section plane A-A (top FIG. 10(*a*)) and a schematic longitudinal sectional view of the bone stabilization implant of FIG. 9 according to the section plane B-B (bottom FIG. 10(*b*))

Referring to FIGS. 7 and 10, the inner face 23 of the stabilization plate 2 is concave according to the longitudinal axis AL, and has a longitudinal radius of curvature RLI which is comprised between 200 and 300 millimeters, and in particular between 230 and 280 millimeters.

The outer face 24 of the stabilization plate 2 is convex according to the longitudinal axis AL, and has a longitudinal radius of curvature RLE substantially equivalent to the longitudinal radius of curvature RLI, and which is therefore comprised between 200 and 300 millimeters, and in particular between 230 and 280 millimeters. Thus, along the longitudinal axis AL, the thickness of the stabilization plate 2 is substantially constant.

Figure 11:
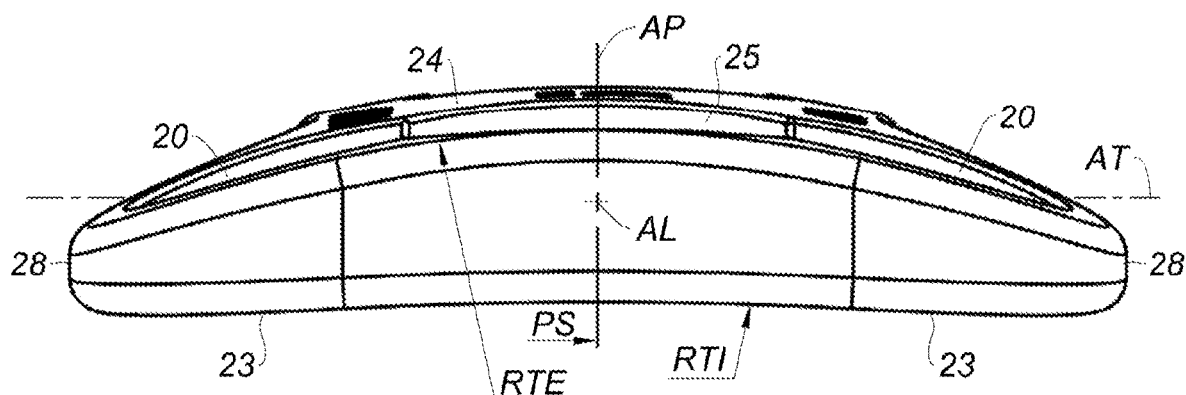
FIG. 11 is a schematic side view of the bone stabilization implant of FIGS. 5 and 6, to visualize the transverse profile of the stabilization plate.

Referring to FIG. 11, considering a transverse axis AT orthogonal to the longitudinal axis AL and to the pivot axis AP, the inner face 23 of the stabilization plate is concave according to the transverse axis AT, and has an inner radius of curvature RTI which is comprised between 60 and 100 millimeters, and in particular between 75 and 85 millimeters.

The outer face 24 of the stabilization plate 2 is convex according to this transverse axis AT, and has an outer radius of curvature RTE according to the transverse axis AT, where this outer radius of curvature RTE is smaller than the inner radius of curvature RTI, and in particular, this outer radius of curvature RTE is comprised between 10 and 30 millimeters, and in particular between 15 and 25 millimeters.

Thus, when measuring a thickness of the stabilization plate 2 between its inner face 23 and its outer face 24 and considering a longitudinal plane of symmetry PS which includes the longitudinal axis AL and which is orthogonal to the transverse axis AT, the thickness of the stabilization plate 2 varies symmetrically on either side of this longitudinal plane of symmetry PS and decreases along the transverse axis AT and starting from the longitudinal plane of symmetry PS to both respective longitudinal borders 28 of the stabilization plate 2, such that the stabilization plate 2 is thinned at the level of both longitudinal borders 28 thereof as shown in FIG. 11, in order to avoid any trauma to the adjacent tissues. As shown in FIG. 11, the stabilization plate 2 has a maximum thickness at the level of the longitudinal symmetry plane PS, and has minimum thicknesses at the level of the two longitudinal borders 28.

Moreover, each locking element 3 is integrally disposed inside a recess 25 provided on the outer face 24 of the stabilization plate 2.

Thus, the stabilization plate 2 has two recesses 25 (of the counterbore or countersunk type), each recess 25 being formed in an end portion 22. Each recess 25 may have a circular shape centered on the concerned pivot axis AP, where this recess 25 projects on both concerned anchor orifices 20, and where the associated locking element 3 has a larger dimension which is substantially smaller than the diameter of this circular recess 25, such that the locking element 3 is mounted in a fitted manner, that is to say with a reduced clearance, inside this recess 25.

Each recess 25 has a planar bottom wall 250, orthogonal to the pivot axis AP, into which opens, at the center thereof, a bore 26 centered on the pivot axis AP and which passes through the stabilization plate 2 to also open into the inner face 23.

Moreover, and as shown in the Figures, the recess 25 opens into the inlet portions 201 of the two anchor orifices 20 such that, in the locking position, the locking element 3 extends into the inlet portions 201 of the two anchor orifices 20, above the bearing faces 202 of the two anchor orifices.

Moreover, each recess 25 has two indexing holes 27 which pass through the stabilization plate 2 to open into the bottom wall 250 and into the inner face 23, where these two indexing holes 27 are disposed on either side of the pivot axis AP according to a direction parallel to the longitudinal axis AL.

Each locking element 3 is mounted only pivotally about the pivot axis AP while being secured in rotation to a pivot shaft 4 pivotally mounted in the bore 26 opening into the concerned recess 25. Each locking element 3 is pivotable at 360 degrees in two opposite directions of rotation (clockwise direction and counterclockwise direction) about the pivot axis AP.

This pivot shaft 4 is inserted from below, that is to say on the side of the inner face 23 of the stabilization plate 2, and it has a head 40 which abuts against an inner shoulder 260 provided in the bore 26, as well as a rod 41 which passes through the bottom wall 250 of the recess 25 without projecting from the outer face 24 of the stabilization plate 2, and on which is fastened the locking element 3.

Thus, each locking element 3 is locked in translation in two opposite directions of translation along the pivot axis AP, with an upward locking provided by the head 40 and a downward locking provided by the locking element 3.

The locking element 3 is more specifically secured in rotation to the rod 41 of the pivot shaft 4, in particular with the rod 41 which is forcibly mounted inside a hole 30 provided at the center of the locking element 3, or alternatively with the locking element 3 which is fastened on the rod 40 by welding, screwing, or another equivalent securement technique or element. Thus, each locking element 3 is securely mounted on the stabilization plate 2, without risk of falling or disengagement during the surgical operation and then all along its implantation in situ on the patient.

The depth (dimension considered parallel to the pivot axis AP) of each recess 25 is larger than the maximum thickness of the locking element 3, such that the locking element 3 does not protrude above the outer face 24 of the stabilization plate 2 irrespective of its position.

Each locking element 3 has a lower face 31 facing the bottom wall 250 of the recess 25 or facing the associated anchor orifice 20 in the locking position, and an opposite upper face 32.

This lower face 31 of the locking element 3 has:

a central area 310 bearing on the bottom wall 250 of the recess 25, irrespective of the position of the locking element 3, where this central area 310 is crossed by the pivot shaft 4;

two peripheral areas 311 adapted to at least partially cover the two associated anchor orifices 20 in the locking position, where these two peripheral areas 311 extend from the central area 310 according to two respective radial axes AR extending radially from the pivot axis AP; and two flanges 34 which extend the respective peripheral areas 311 and at least partly define a border of the locking element 3.

Figure 8:
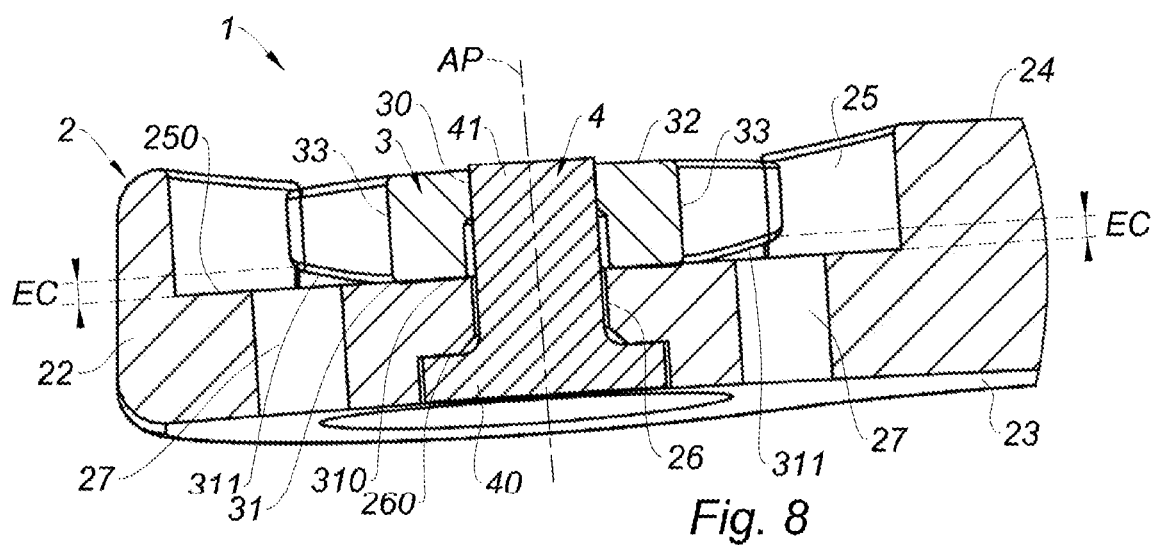
FIG. 8 is a schematic enlarged view on the area VIII of FIG. 7.
Figure 9:
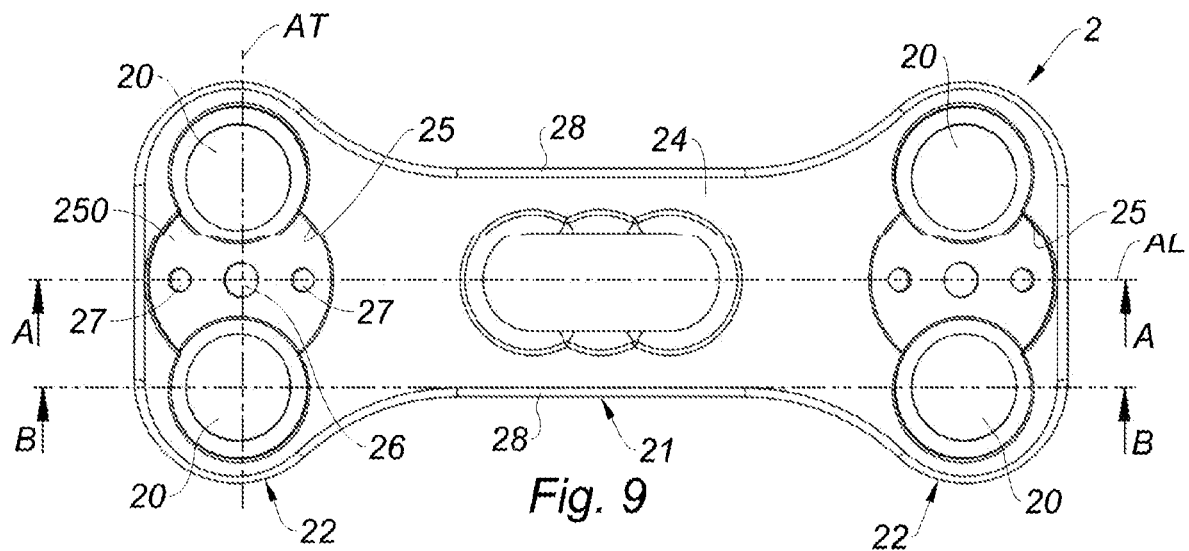
FIG. 9 is a schematic top view of the bone stabilization implant of FIGS. 5 and 6, without the two locking elements.

Each of the two peripheral areas 311 of this lower face 31 of the locking element 3 has a convex shape according to both radial axes AR extending radially from the pivot axis AP to both peripheral areas 311, such that, in the rest position, each of the two peripheral areas 311 of this lower face 31 deviates from the bottom wall 250 of the recess 25 starting from the central area 310 which is in contact with this bottom wall 250 to each flange 34 which is deviated from the bottom wall 250 by a deviation EC (as shown in FIG. 8 in the example of the first form).

When measuring a thickness of the locking element 3 between its lower face 31 and its upper face 32, the thickness of the locking element 3 decreases along the radial axes and starting from the central area 310 of the lower face 31 to the peripheral areas 311 then to the flanges 34 of the lower face 31, such that the locking element 3 is thinned at the level of the flanges 34.

Figure 14:
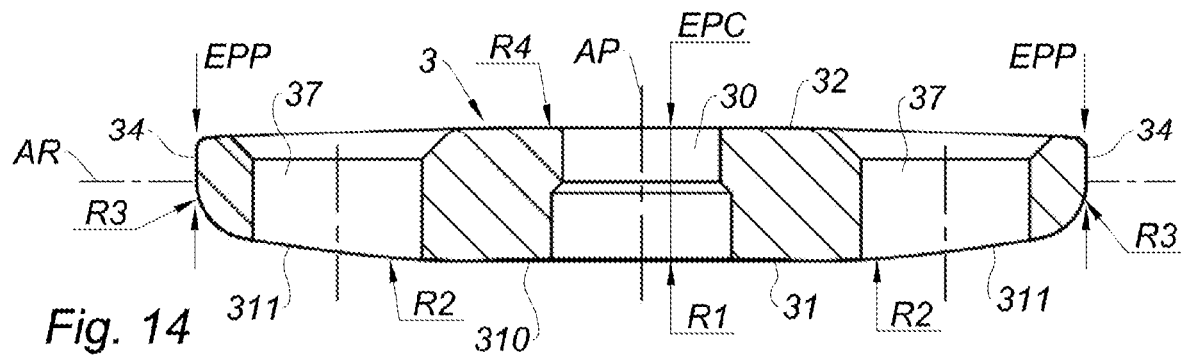
FIG. 14 is a schematic sectional view of the locking element of FIG. 13 according to the section plane C-C.
Figure 15:
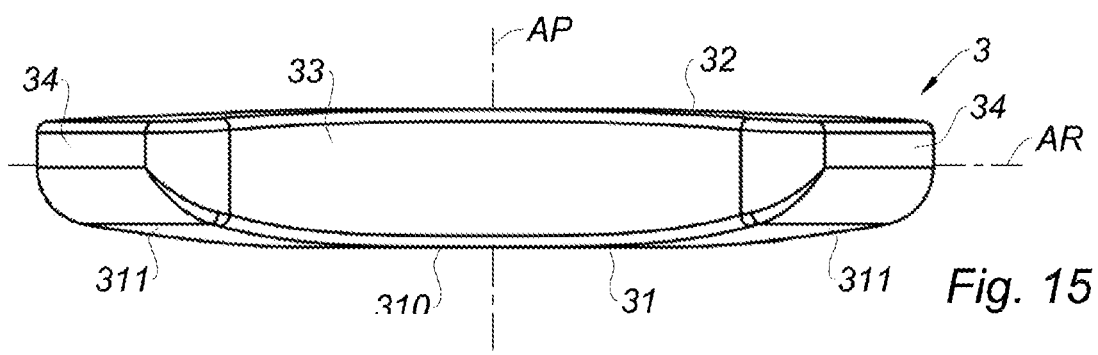
FIGS. 15 and 16 are schematic side views of the locking element of FIG. 13.
Figure 16:
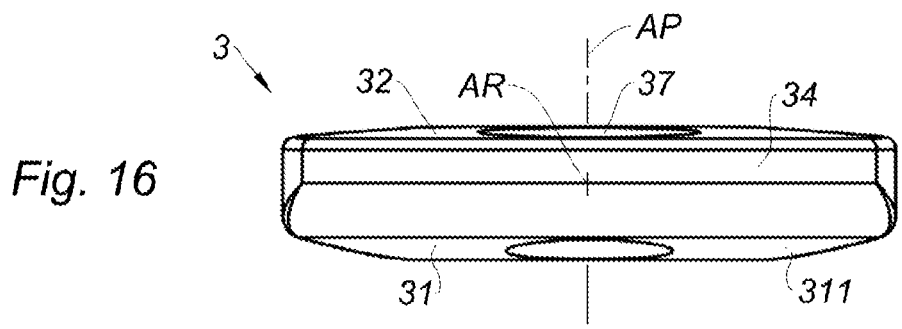

As shown in FIG. 14 in the example of the first form, the locking element 3 has a thickness EPC at the level of the central area 310 which is maximum, and has thicknesses EPP at the level of the flanges 34 which are smaller than the thickness EPC, and which are even minimum.

As shown in FIG. 14 in the example of the first form, the lower face 31 of the locking element 3 has, according to each radial axis AR:

a first radius of curvature R1 on its central area 310, which is comprised between 30 and 60 millimeters, and in particular between 40 and 50 millimeters, and where this first radius of curvature R1 can be concave or convex;

a second radius of curvature R2 on its two peripheral areas 311, in the continuation of the first radius of curvature R1 of the central area 310, which is smaller than the first radius of curvature R1 and which is comprised between 5 and 20 millimeters, and in particular between 8 and 15 millimeters, where this second radius of curvature R2 is convex; and a third radius of curvature R3 on the flanges 34 such that these flanges 34 form rounded chamfers, in the continuation of the two peripheral areas 311 of the second radius of curvature R2, where this third radius of curvature R3 is smaller than the second radius of curvature R2 and is comprised between 0.4 and 1 millimeter, and in particular in the range of 0.5 millimeter, and where this third radius of curvature R3 is convex.

The lower face 31 extends over a given main distance DP starting from the pivot axis AP, and along each radial axis AR, and:

the central area 310 extends from the pivot axis AP along the radial axis AR, over a central distance DC such that the ratio DC/DP is comprised between 0.1 and 0.3;

the peripheral area 311 extends from the central area 310 along the radial axis AR, over a peripheral distance DH such that the ratio DH/DP is comprised between 0.5 and 0.7;

the flange 34 extends from the peripheral area 311 along the radial axis AR, over an edge distance DB such that the ratio DB/DP is comprised between 0.1 and 0.2;

and where DP=DC+DH+DB.

As shown in FIG. 14 in the example of the first form, the upper face 32 has a convex shape according to the radial axis AR. This upper face 32 has a radius of curvature R4 which is larger than the second radius of curvature R2 and which is comprised between 30 and 60 millimeters, and in particular between 40 and 50 millimeters.

In the first form of FIGS. 1 to 23, the locking element 3 has a disk-like general shape centered on the pivot axis AP, where the pivot axis AP intersects the transverse axis AT and the longitudinal axis AL, at the midway between the two anchor orifices 20, such that the recess 25 and the locking element 3 are both provided between the two anchor orifices 20.

Moreover, in the first form, the locking element 3 has indentations 33 that are diametrically opposite to each other on either side of the pivot axis AP; each of these indentations 33 having a concave and arcuate shape according to a diameter substantially equivalent to the largest diameter of the anchor orifices 20. The two peripheral areas 311 of the lower face 31 of the locking element 3 are in turn disposed at the level of the two bulging flanges 34 (or rounded chamfers) which are diametrically opposite to each other on either side of the pivot axis AP, and which are surrounded by the indentations 33. These two bulging flanges 34 are thinned, as described above.

Thus, in the first form, the two peripheral areas 311 of the lower face 31 of the locking element 3 are also disposed diametrically opposite to each other on either side of the pivot axis AP, and these two peripheral areas 311 are offset at 90 degrees, about the pivot axis AP, relative to the indentations 33. In this first form, the two radial axes AR starting from the pivot axis AP to both respective peripheral areas 311 are therefore coincident on the same radial axis AR.

Figure 5:
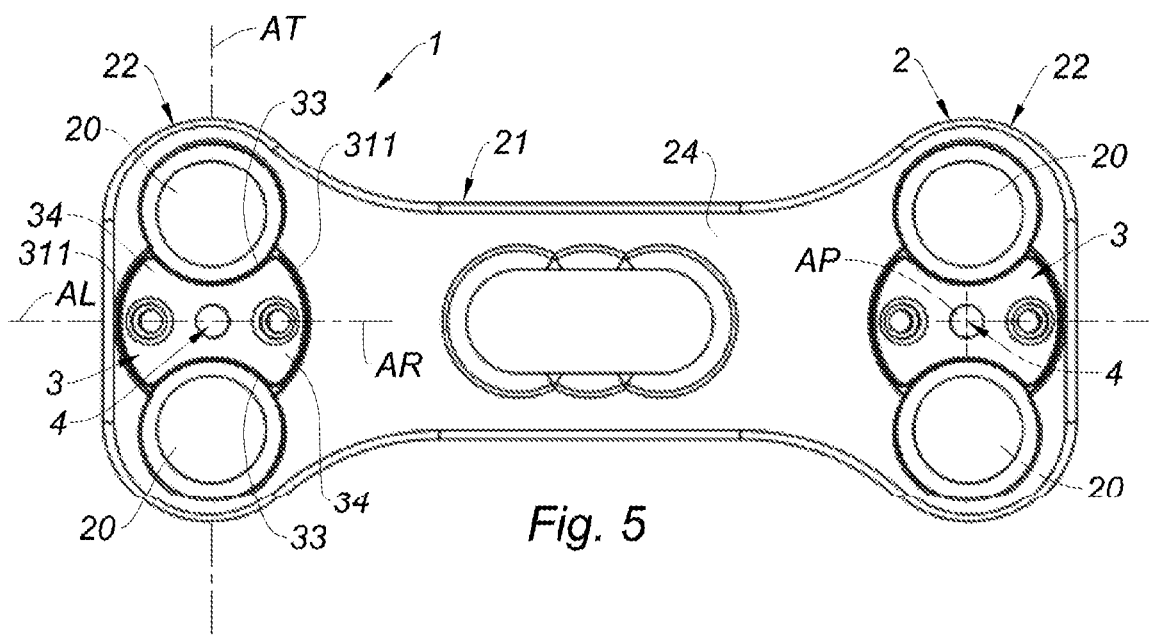
FIGS. 5 and 6 are schematic top views of the bone stabilization implant of FIG. 3, with two locking elements in the rest position (FIG. 5) and in the locking position (FIG. 6)
Figure 6:
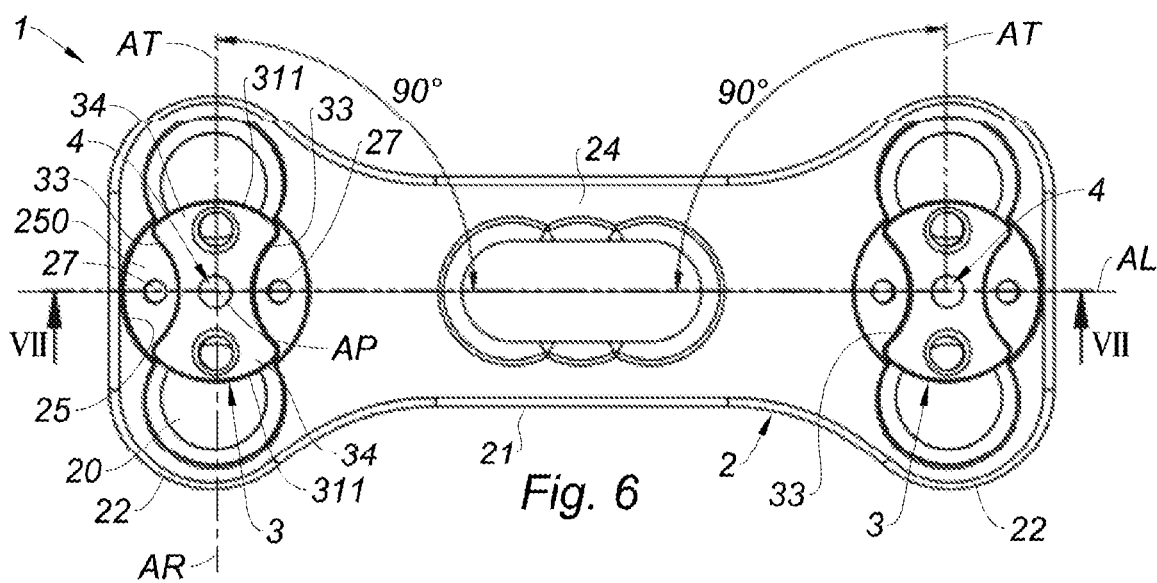

In the rest position (as shown in FIG. 5), the indentations 33 conform to the anchor orifices 20, whereas the bulging edges 34 conform to the inner periphery of the recess 25. In this rest position, the radial axis AR (common to both peripheral areas 311) is parallel to the longitudinal axis AL.

Starting from the rest position, a pivoting by 90 degrees (in either direction) switches the locking element 3 into the locking position, which brings the two bulging flanges 34 above the anchor orifices 20, and therefore the peripheral areas 311 partially cover the two associated anchor orifices 20. In this locking position, the radial axis AR (common to both peripheral areas 311) is parallel to the transverse axis AT.

It should be noted that, in the first form, the locking element 3 is provided with two holes 37 on its upper face 32 to enable a handling and a pivoting by a tool such as a clamp. These two holes 37 are disposed on either side of the pivot axis AP according to the radial axis AR. Advantageously, these two holes 37 are through-holes to open into the lower face 31, and furthermore, in the rest position, these two holes 37 coincide with the two indexing holes 27 formed in the bottom wall 250 of the corresponding recess 25.

In the second form of FIGS. 24 and 25, the locking element 3 differs from that of the first form only in its shape, namely an elongated body shape according to the radial axis and having two rectilinear longitudinal edges 35 (instead of the two arcuate indentations 33) and two rounded end edges 36 (equivalent to the bulging flanges 34). These two end edges 36 are thinned, as previously described.

In the third form, the locking element 3 has a half-disk general shape centered on the pivot axis AP, where the pivot axis AP intersects the longitudinal axis AL and is away from the transverse axis AT by a distance DA along the longitudinal axis AL, and where the pivot axis AP and the longitudinal axis AL define a midplane PM passing through the pivot axis AP, orthogonal to the transverse axis AT and crossing this transverse axis AT at the midway between the two anchor orifices 20.

In this third form, the locking element 3 has a semicircular external border 38 and the lower face of the locking element 3 has two peripheral areas 311 at the level of this external border 38, where these two peripheral areas 311 are disposed on either side of the midplane PM without being diametrically opposite to each other with respect to the pivot axis AP, such that the two radial axes AR starting from the pivot axis AP to both respective peripheral areas 311 form a non-zero angle AN at their intersections on the pivot axis AP. This external border 38 is thinned as previously described.

In the rest position (as shown in FIG. 27), the locking element 3 is stowed with its external border 38 turned opposite to the anchor orifices 20; where this external border 38 conforms to the inner periphery of the recess 25. In this rest position, the two radial axes AR substantially pass through the respective centers of the anchor orifices 20, and the two peripheral areas 311 are diametrically opposite to the respective anchor orifices 20 on either side of the pivot axis AP.

Starting from the rest position, a pivoting by 180 degrees (in either direction) switches the locking element 3 into the locking position (as shown in FIG. 26), which causes the two peripheral areas 311 to rotate by 180 degrees and therefore to partially cover the two associated anchor orifices 20. In this locking position, the two radial axes AR substantially pass through the respective centers of the anchor orifices 20.

Regardless of the form, in place, the bone anchor screws 9 can:

be inserted into the anchor orifices 20 when the locking elements 3 are in the rest position; and be locked in the anchor orifices 30 and thus be inhibited from coming out beyond the outer face 24 of the stabilization plate 2 when the locking elements 3 are in the locking position.

It should be noted that the locking elements 3 are intended to inhibit inadvertent back-outs of the bone anchor screws 9 and not to exert a force ensuring the tightening of the bone anchor screws 9.

Each locking element 3 has a convexity on the lower face 31 according to the radial axis or axes AR in order to wisely use the elastic effect of the deformation to keep it stable on the stabilization plate 2 irrespective of its position. Each locking element 3 is also remarkable in that its handling is done by rotation independently of the direction of rotation and without restricting its function of inhibiting the back-out of the bone anchor screws 9.

In other words, each locking element 3 is remarkable in that its design and mounting enable it to use the elasticity properties of the material to remain in the locking position, with its convexity on the lower face 31 according to the radial axis or axes AR.

Such a concavity is used to mount and connect the locking element 3 to the stabilization plate 2 in the final locking position, the peripheral areas 311 being housed within the anchor orifices 20 because of the concavity, and these peripheral areas 311 then coming into frictional contact on the stabilization plate 2 when placed in the rest position, which has the effect of elastically bending the locking element 3.

This arrangement therefore allows using the elasticity stored by the locking element 3 to provide a self-stable position in the locking position on the bone anchor screws 9.

As shown in FIGS. 18 and 19 for the first form, thanks to the conformation of the locking elements 3, the bone anchor screws 9 have angular displacements of their respective screwing axes AV at 360 degrees about the central axes of the anchor orifices 20 (as a reminder, these central axes form the axes of symmetry of the bearing faces 202 of the anchor orifices).

In other words, for each bone anchor screw 9, the screwing axis AV can be inclined, with respect to a neutral position, by plus or minus a maximum angular displacement; the neutral position of a bone anchor screw 9 corresponding to a position in which the screwing axis AV coincides with the central axis of the corresponding anchor orifice 20. This maximum angular displacement is advantageously in the range of 5 to 15 degrees.

Thus, the bone anchor screws 9 may have different inclinations of their respective AV screwing axes, and in particular:

as shown in FIG. 19, a longitudinal inclination according to the longitudinal axis AL, with a longitudinal angular displacement DL which can be at most in the range of 5 to 15 degrees;

as shown in FIG. 18, a transverse inclination according to a transverse axis AT, with a transverse angular displacement DT which can be at most in the range of 5 to 15 degrees.

Unless otherwise expressly indicated herein, all numerical values indicating mechanical/thermal properties, compositional percentages, dimensions and/or tolerances, or other characteristics are to be understood as modified by the word "about" or "approximately" in describing the scope of the present disclosure. This modification is desired for various reasons including industrial practice; material, manufacturing, and assembly tolerances; and testing capability.

As used herein, the phrase at least one of A, B, and C should be construed to mean a logical (A OR B OR C), using a non-exclusive logical OR, and should not be construed to mean "at least one of A, at least one of B, and at least one of C."

The description of the disclosure is merely exemplary in nature and, thus, variations that do not depart from the substance of the disclosure are intended to be within the scope of the disclosure. Such variations are not to be regarded as a departure from the spirit and scope of the disclosure.

The invention claimed is:

1. A bone stabilization implant for stabilizing at least two bone structures, said bone stabilization implant comprising:
    a stabilization plate provided with an inner face intended to be in contact with the bone structures and an opposite outer face, with at least two anchor orifices which pass through said stabilization plate from the inner face to the outer face, said anchor orifices being intended to receive bone anchor screws for anchorage in the bone structures;
    at least one locking element associated with two anchor orifices aligned according to a transverse axis, said locking element being pivotally mounted on the outer face of the stabilization plate about a pivot axis orthogonal to the transverse axis, between a rest position in which the locking element completely uncovers the two associated anchor orifices and a locking position in which the locking element at least partially covers the two associated anchor orifices, in place, to lock the bone anchor screws in said two anchor orifices and thus inhibit the bone anchor screws from coming out beyond the outer face of the stabilization plate, and in which said locking element has a lower face facing the associated anchor orifice and an opposite upper face;
    wherein:
    each of the two anchor orifices is at least internally delimited, starting from the outer face to the inner face, successively by an inlet portion with a cylindrical shape followed by a bearing face shaped as a spherical or frustoconical portion to enable a bearing with polyaxiality to the corresponding bone anchor screw;
    the locking element is mounted pivotally about the pivot axis being secured in rotation to a pivot shaft pivotally mounted in a bore formed in the stabilization plate, said locking element being pivotable at 360 degrees in two opposite directions of rotation about the pivot axis;
    the locking element is integrally disposed inside a recess provided on the outer face of the stabilization plate such that the locking element does not protrude above the outer face of the stabilization plate irrespective of its position;
    the locking element is locked in translation in two opposite directions of translation along the pivot axis, said pivot shaft having a head which abuts against an inner shoulder provided in the bore as well as a rod which passes through a bottom wall of the recess without projecting from the outer face of the stabilization plate, and on which is fastened the locking element;
    the recess opens into the inlet portions of the two anchor orifices such that, in the locking position, the locking element extends into the inlet portions of the two anchor orifices, above the bearing faces of the two anchor orifices;
    the lower face of the locking element has a central area bearing on the bottom wall of the recess and crossed by the rod of the pivot shaft, and said lower face has two peripheral areas adapted to at least partially cover the two respective associated anchor orifices in the locking position, said two peripheral areas extending from the central area to respective flanges, according to two respective radial axes extending radially from the pivot axis;
    the two peripheral areas of the lower face of the locking element have a convex shape according to both respective radial axes from the central area to the respective flanges such that, in the rest position, each of the two peripheral areas of the lower face deviates from the bottom wall of the recess starting from the central area which is in contact with said bottom wall to the flanges which are deviated from said bottom wall;
    the two peripheral areas of the lower face of the locking element have, according to each of the two radial axes, a second radius R2 of curvature.

2. The bone stabilization implant according to claim 1, wherein the second radius of curvature R2 on both peripheral areas, along the respective radial axes, is between 5 and 20 millimeters.

3. The bone stabilization implant according to claim 1, wherein the central area has a convex or concave shape according to a first radius of curvature R1, wherein the second radius of curvature R2 is smaller than the first radius of curvature R1.

4. The bone stabilization implant according to claim 3, wherein the first radius of curvature R1 is between 30 and 60 millimeters.

5. The bone stabilization implant according to claim 1, wherein the lower face of the locking element has a symmetry of revolution about the pivot axis.

6. The bone stabilization implant according to claim 1, wherein the flanges of the lower face form rounded chamfers, in the continuation of the two peripheral areas, having a third radius of curvature R3 which is smaller than the second radius of curvature R2.

7. The bone stabilization implant according to claim 6, wherein the third radius of curvature R3 is between 0.4 and 1 millimeter.

8. The bone stabilization implant according to claim 1, wherein the lower face extends over a given main distance starting from the pivot axis, and along each radial axis, and successively has:

the central area which extends from the pivot axis along the radial axis, over a given central distance such that the ratio of the central distance to the main distance is between 0.1 and 0.3;

the peripheral area which extends from the central area along the radial axis, over a peripheral distance such that the ratio of the peripheral distance to the main distance is between 0.5 and 0.7;

the flange which extends from the peripheral area along the radial axis, over an edge distance such that the ratio of the edge distance to the main distance is between 0.1 and 0.2;

and wherein the main distance is equivalent to the sum of the central distance, the peripheral distance and the edge distance.

9. The bone stabilization implant according to claim 1, wherein when measuring a thickness of the locking element between its lower face and its upper face, the thickness of the locking element decreases along the two radial axes and from the central area of the lower face, then along the peripheral areas to the flanges of the lower face, such that the locking element is thinned at the level of the flanges.

10. The bone stabilization implant according to claim 1, wherein the upper face of the locking element has a convex shape according to both radial axes.

11. The bone stabilization implant according to claim 1, wherein the upper face of the locking element has a symmetry of revolution about the pivot axis.

12. The bone stabilization implant according to claim 1, wherein the two peripheral areas of the lower face of the locking element are disposed diametrically opposite to each other on either side of the pivot axis, such that the two radial axes starting from the pivot axis to both respective peripheral areas are coincident.

13. The bone stabilization implant according to claim 1, wherein the two peripheral areas of the lower face of the locking element are disposed on either side of a midplane passing through the pivot axis and orthogonal to the transverse axis without being diametrically opposite to each other, such that the two radial axes starting from the pivot axis to both respective peripheral areas form a non-zero angle at their intersections on the pivot axis.

14. The bone stabilization implant according to claim 1, wherein the stabilization plate has an elongated shape according to a longitudinal axis, and the inner face of the stabilization plate is concave according to said longitudinal axis and the outer face of the stabilization plate is convex according to said longitudinal axis.

15. The bone stabilization implant according to claim 14, wherein the transverse axis is orthogonal to the longitudinal axis and to the pivot axis, and the inner face of the stabilization plate is concave according to said transverse axis and the outer face of the stabilization plate is convex according to said transverse axis.

16. The bone stabilization implant according to claim 15, wherein the inner face of the stabilization plate has an inner radius of curvature according to the transverse axis and the outer face of the stabilization plate has an outer radius of curvature according to the transverse axis, wherein the outer radius of curvature is smaller than the inner radius of curvature, and when measuring a thickness of the stabilization plate between its inner face and its outer face and considering a longitudinal plane of symmetry which includes the longitudinal axis and which is orthogonal to the transverse axis, the thickness of the stabilization plate varies symmetrically on either side of said longitudinal plane of symmetry and decreases according to the transverse axis and starting from the longitudinal plane of symmetry to both respective longitudinal borders of the stabilization plate, such that the stabilization plate is thinned at the level of both longitudinal borders thereof.

17. The bone stabilization implant according to claim 1, wherein the locking element is provided with two holes on its upper face to enable a handling and a pivoting by a tool.

18. The bone stabilization implant according to claim 1, wherein the bone stabilization implant is a cervical spine stabilization implant.

19. A bone stabilization system for stabilizing at least two bone structures, said bone stabilization system comprising at least:

one bone stabilization implant according to claim 1; and at least two bone anchor screws, with a bone anchor screw per anchor orifice formed in the stabilization plate of the bone stabilization implant, where the bone anchor screws are configured to:

be inserted into the anchor orifices when the locking element is in the rest position; and be locked in the anchor orifices and thus be prevented from coming out beyond the outer face of the stabilization plate when the locking element is in the locking position;

wherein each of the bone anchor screws has a head having a spherical bearing surface to bear with polyaxiality on the bearing face of the concerned anchor orifice, and a threaded rod adapted to be anchored in the concerned bone structure and extending according to a screwing axis, such that the bone anchor screws have angular displacements of their respective screwing axes at 360 degrees, and the locking element provides a locking of the two bone anchor screws irrespective of the angular displacements of their respective screwing axes.

20. The bone stabilization system according to claim 19, wherein the bone anchor screws have angular displacements of between 5 to 15 degrees.

* * * * *